United States Patent
Bailly et al.

[11] Patent Number: 5,336,202
[45] Date of Patent: Aug. 9, 1994

[54] ATTACHMENT FOR A SYRINGE FOR SPRAYING MIXTURES OF FLUIDS

[76] Inventors: Alain Bailly, 20, rue du Bois des Roches, 91700 Sainte Genevieve Des Bois, France; Gérard Ramsteiner, L'Orme Rond-RN19, 77170 Servon, France; Michel Saurou, Courbevoie, all of France

[21] Appl. No.: 988,953
[22] PCT Filed: Sep. 17, 1991
[86] PCT No.: PCT/FR91/00730
§ 371 Date: Mar. 10, 1993
§ 102(e) Date: Mar. 10, 1993
[87] PCT Pub. No.: WO92/04878
PCT Pub. Date: Apr. 2, 1992

[30] Foreign Application Priority Data
Sep. 20, 1990 [FR] France .................. 90 11605

[51] Int. Cl.⁵ .................................................. A61M 5/31
[52] U.S. Cl. .................................. 604/240; 604/242; 604/258; 433/88
[58] Field of Search .............. 433/80, 81, 88, 89; 604/187, 191, 239, 240, 242, 243, 258, 264, 199, 39, 43; 128/66

[56] References Cited

U.S. PATENT DOCUMENTS

| | | | |
|---|---|---|---|
| 3,137,297 | 7/1961 | Maurer et al. | 128/173.1 |
| 3,753,435 | 8/1973 | Blasnik | 128/66 |
| 3,810,465 | 5/1974 | Lambert | 128/66 |
| 3,972,123 | 8/1976 | Black | 433/88 |
| 4,519,385 | 5/1985 | Atkinson et al. | 128/66 |
| 4,522,597 | 6/1985 | Gallant | 433/88 |
| 4,613,329 | 9/1986 | Bodicky | 604/243 |
| 4,735,200 | 4/1988 | Westerman | 128/66 |
| 4,957,483 | 9/1990 | Gonser et al. | 433/80 |
| 4,984,984 | 1/1991 | Esrock | 433/88 |

FOREIGN PATENT DOCUMENTS

| | | | |
|---|---|---|---|
| 0052736 | 6/1982 | European Pat. Off. | 128/66 |
| 0358272 | 9/1989 | European Pat. Off. | A61C 17/02 |
| 1416921 | 4/1960 | Fed. Rep. of Germany . | |
| 1283435 | 11/1968 | Fed. Rep. of Germany | 433/80 |
| 2621809 | 10/1988 | France | A61C 17/02 |
| 2639534 | 11/1988 | France | A61C 17/02 |
| WO90/07912 | 8/1989 | PCT Int'l Appl. | A61C 17/02 |
| 1450827 | 1/1989 | U.S.S.R. | 604/191 |

*Primary Examiner*—C. Fred Rosenbaum
*Assistant Examiner*—Frank Wilkens
*Attorney, Agent, or Firm*—W. Thad Adams, III

[57] ABSTRACT

The equipment consists, on the one hand, of a metallic adaptor (2) having an upstream end (10) which can be connected to the syringe and a downstream end (9) which can be connected to a disposable cannula (1), the said cannula (1) defining at least two channels (5, 6) for distribution of fluid, and the said adaptor (2) comprising a corresponding number of supply channels (18, 19) which can be brought into correspon-dence, for communication of fluid, with the said distri-bution channels (5, 6).

According to the invention, the cannula (1) is made of moulded plastic material, the distribution channels (5, 6) are of constant cross-section at least over almost the whole of their length, and tubular sleeves (25, 26), connected to the said supply channels (18, 19), project from the downstream end face (37) of the said adaptor (2), the relative position and the dimensions of the said tubular sleeves (25, 26) being such that they are designed to be received, each one, in the upstream end of a distribution channel (5, 6).

8 Claims, 2 Drawing Sheets

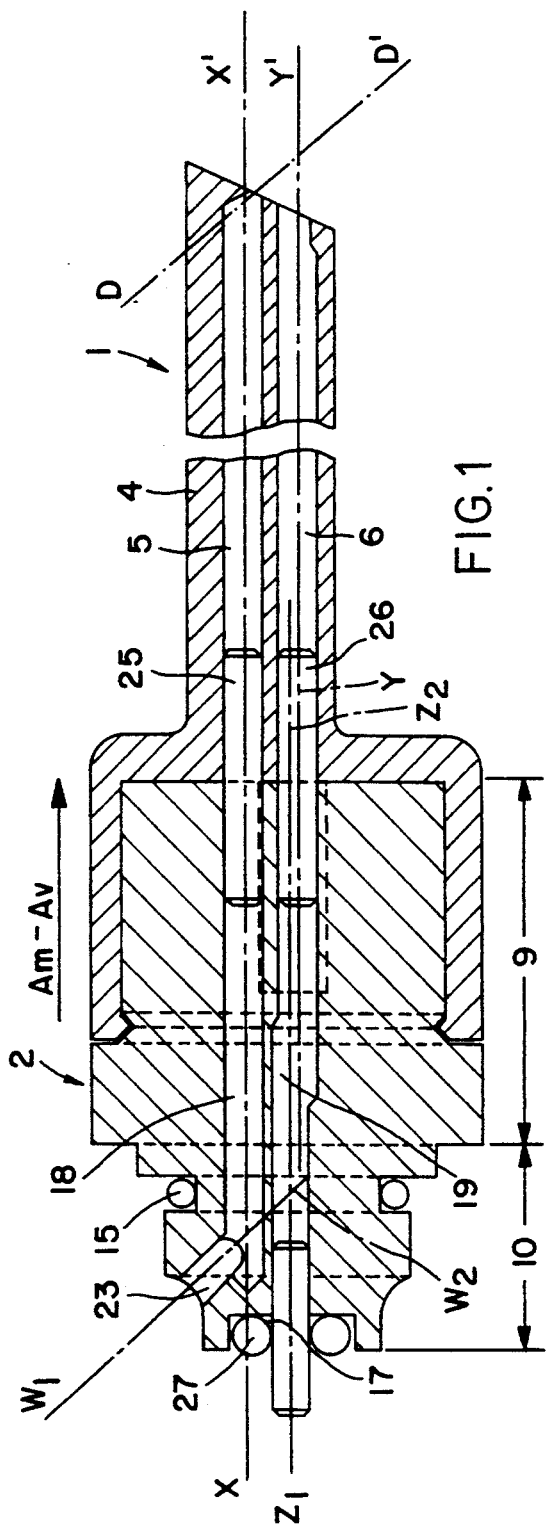
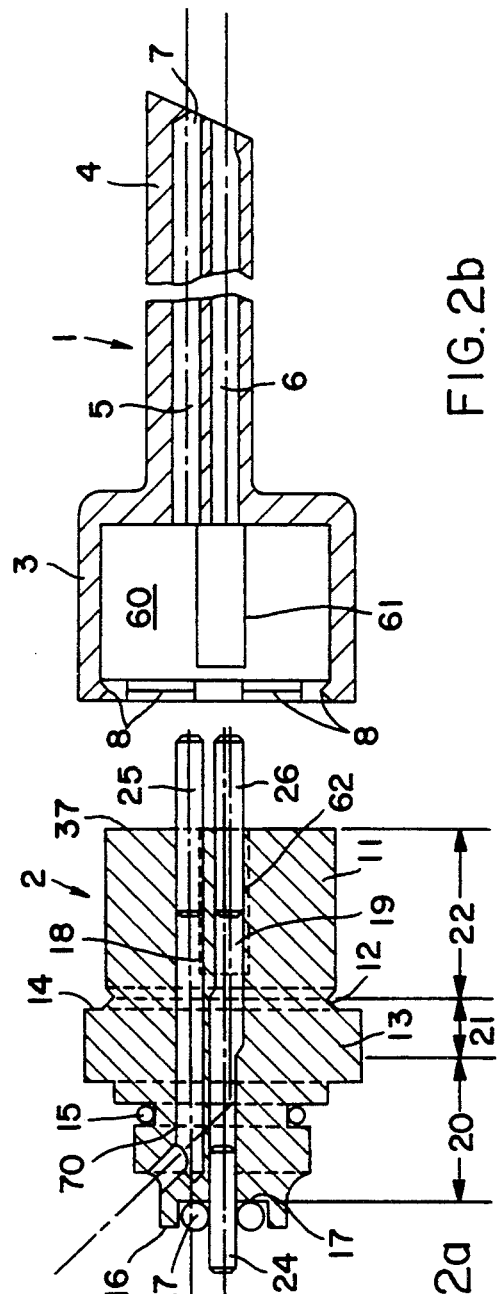

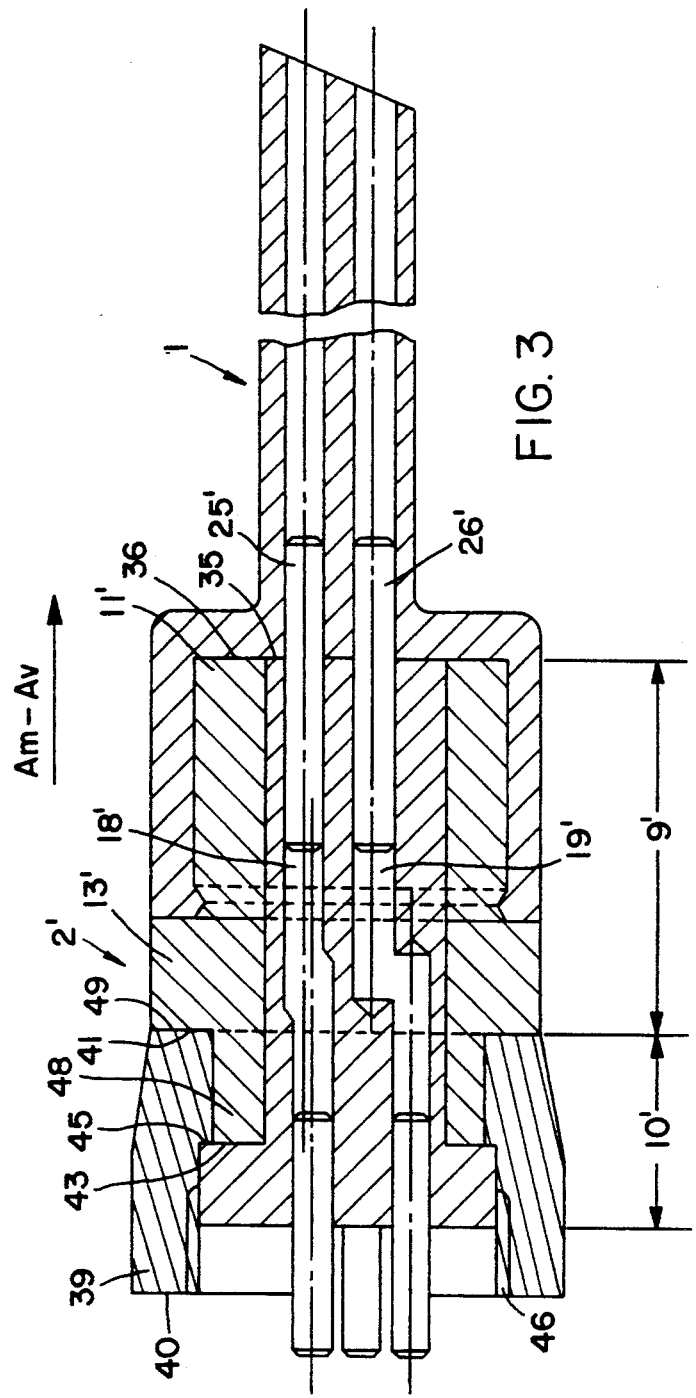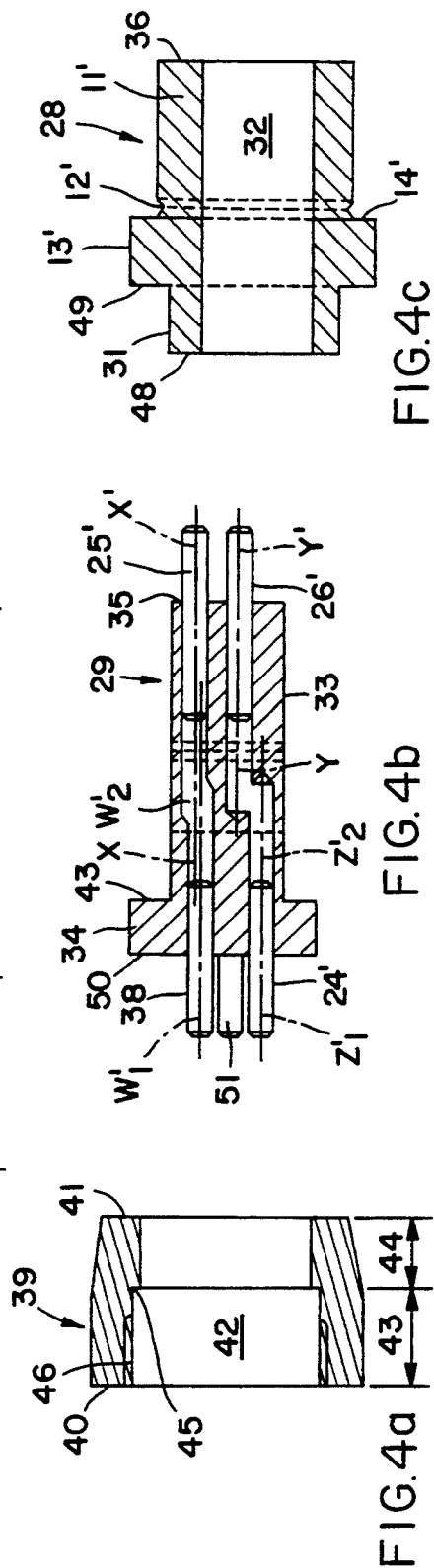

ATTACHMENT FOR A SYRINGE FOR SPRAYING MIXTURES OF FLUIDS

This application is a PCT application.

The present invention relates to equipment for syringes for spraying mixtures of fluids as used, in particular, in dentistry.

At the present time, in order to spray a mixture of air and of water onto the site of the dental operation, or one of the two fluids alone, use is made of equipment consisting of a syringe (of various models) and of corresponding cannulas whose free end is introduced into the patient's mouth. These cannulas, which are reusable, are of course soiled while being used, and it is essential to sterilise them after use.

However, the trend in the medical field in general, and in the dental field in particular, is to employ disposable instruments and tools in order, on the one hand, to do away with the need for laborious sterilisation after each use and, on the other hand, to give a sense of security to the patient—and in some cases the attendant personnel—fearing contamination from previously soiled instruments.

Equipment has already been proposed, which consists of a metallic adaptor having, viewed in the direction of flow of the fluids, an upstream end which can be connected to the syringe and a downstream end which can be connected to a disposable cannula, the said cannula defining at least two fluid-distribution channels which extend side by side, and the said adaptor comprising a corresponding number of supply channels which can be brought into correspondence, for communication of fluid, with the said distribution channels.

Thus, FR-A-2 639 534 HEUILLON proposes equipment comprising a disposable cannula, of which the constituent material is not specified, and an adaptor. Two supply channels of circular cross-section are formed side by side in the solid material of the adaptor, which also has a circular cross-section, but one which is considerably larger than that of the supply channels. For its part, the cannula has two distribution channels defined by a cavity of circular cross-section decreasing rapidly from upstream to downstream and divided diametrically by a partition, in such a way that the distribution channels have a substantially semicircular and decreasing cross-section. Upstream of the partitioned cavity, the cannula defines a socket designed to receive the downstream end of the adaptor. This downstream end is slotted in a diametral plane equidistant from the two supply channels, the purpose of the slot being to accommodate the abovementioned partition when the cannula is fitted onto the adaptor.

Such a device has a number of disadvantages, most of which are associated with the considerable difference in flow cross-section between the downstream end of the supply channels and that, more than fifteen times larger, of the upstream end of the distribution channels.

The results are that:
until an equilibrium is achieved, the movement of the fluids is turbulent, and their discharge at the end of the cannula is irregular;
when a liquid, for example water, is sprayed, a reserve of water is formed in the cannula, so that, when the practitioner cuts off the supply of water, the flow does not stop immediately and the cannula drips; for the same reason, if the practitioner changes from spraying water to spraying air, for example in order to dry a composite substance, the air, due to the Venturi effect, aspirates the residual water in the neighbouring channel, and it is humid air which is directed onto the preparation to be dried.

In addition, the turbulence effect mentioned above, on account of the forces resulting therefrom, risks causing the untimely disconnection of the cannula and the adaptor.

Finally, it is fairly unlikely that the proposed cannula could be made of moulded plastic material, since it is difficult to see how the demoulding would be carried out.

Another solution has been proposed in WO90/07912 SEGAL. This time, the supply channels of the adaptor and the corresponding distribution channels of the cannula are not juxtaposed side by side, but instead are coaxial. The manufacture of such cannulas is all the more complicated by the fact that it is intended to provide them with a bayonet socket for their connection to the adaptor, with a view to preventing the disconnection mentioned hereinabove. Such a structure necessitates a manufacturing method whose cost is difficult to reconcile with the production of a disposable article, so that it is to be feared that, given the price, the disposable cannulas are in fact reused.

The aim of the present invention is to overcome the disadvantages of both the known equipment types, this aim being achieved to the extent that the invention provides equipment of the abovementioned type, characterised in that the said cannula is made of moulded plastic material, in that the said distribution channels are of constant cross-section at least over almost the whole of the length of the cannula, and in that tubular sleeves, called "outlet" sleeves, connected to the said supply channels project from the downstream end face of the said adaptor, the relative position and the dimensions of the said tubular outlet sleeves being such that they are designed to be received, each one, in the upstream end of a distribution channel.

Such a cannula can be manufactured by injection moulding under extremely economical conditions compatible with the desired disposable nature of the product. The connection of the supply channels and the distribution channels by means of the tubular outlet sleeves has proven to be perfectly satisfactory, no untimely separation having been observed in the course of a large number of tests carried out on the equipment according to the invention.

In a manner known per se, the cannula defines a connection socket in the bottom of which the upstream end of the distribution channels opens out, and this socket is capable of fitting on a downstream end part of the adaptor. However, unlike the prior art, at the level of their connection the flow cross-section of the supply channels is substantially equal to the flow cross-section of the distribution channels.

In order to facilitate the mutual orientation of the cannula and of the adaptor at the moment of their connection, the inner face of the peripheral wall of the said socket and the outer peripheral face of the downstream end part of the adaptor can have an axial rib and an axial recess of complementary geometry, respectively, or vice versa, designed to come into engagement.

In a preferred embodiment, the inner face of the peripheral wall of the socket has, in the vicinity of its free edge, a series of regularly spaced and elastically deformable projections, and the lateral wall of the adaptor has a peripheral groove designed to receive the said projections. The engagement of the projections in the groove confirms to the practitioner that he has fitted the cannula sufficiently onto the adaptor, and this eliminates, as required, the extremely low risks of disconnection. Since the projections are elastically deformable, it suffices for the practitioner to pull on the cannula, after use, in order to separate it from the adaptor and discard it.

As has been seen hereinabove, the equipment is used in general for spraying a mixture of air and of water and, consequently, the cannula will define two distribution channels. However, it is possible to imagine applications where more than two fluids will be sprayed, in which case it will be possible for the cannula to define more than two channels.

The channels will generally be juxtaposed in parallel and, so that the fluids are mixed, the profile of the downstream end of at least one of the distribution channels is such that the fluid distributed via this channel converges on the fluid distributed via the other channel.

The free end of at least one of the distribution channels is preferably narrowed in order to increase the spray pressure.

The adaptor must take account of the various syringe models, and various adaptor models will therefore have to be provided: these models will of course have a part with constant geometry, cooperating with the single-model cannula, and a part with a geometry depending on the syringe model.

Thus, in a first embodiment of the invention, suitable, for example, for the Adec and Hanau syringe models, the adaptor comprises, on the one hand, a tubular inlet element which projects from the upstream end face of the said adaptor and which is connected to one of the supply channels, in order to convey a first fluid towards one of the tubular outlet sleeves, the said tubular inlet sleeve being parallel to the longitudinal axis of the adaptor and, on the other hand, an inlet passage for a second fluid opening, on the one hand, into the upstream end face of the said adaptor and, on the other hand, into another supply channel connected to the other tubular outlet sleeve, the said inlet passage forming an angle with the longitudinal axis of the adaptor.

In another embodiment, suitable, for example, for Lucciani syringes, the adaptor comprises two tubular inlet sleeves and a corrector parallel to the longitudinal axis of the adaptor and projecting from the upstream end face of the latter, the two inlet sleeves each being in fluid communication with a tubular outlet sleeve, and the corrector penetrating into a cul-de-sac passage formed in the adaptor.

In this model, the adaptor preferably consists of a muff, whose geometry and outer dimensions are designed to allow it to be received in the socket of the cannula, and of a core in which are formed the supply channels provided with their tubular sleeves.

Other characteristics and advantages of the invention will emerge from the description which follows and in which reference is made to the attached drawings, in which:

FIG. 1 is a longitudinal cutaway view of the equipment according to a first embodiment of the invention, FIGS. 2a and 2b show on a smaller scale, in longitudinal section and in the separated state, the components of the embodiment in FIG. 1, FIG. 3 is a longitudinal cutaway view of the equipment according to a second embodiment of the invention, FIGS. 4a, 4b and 4c show on a smaller scale, in longitudinal section and in the separated state, the components of the embodiment in FIG. 3, with the exception of the cannula, since the latter is identical to that in FIG. 2b.

First of all, it should be pointed out that in the present description, and in the claims, the terms upstream and downstream which are used refer to the direction of flow of the fluids as indicated by the arrow Am-Av in FIGS. 1 and 3.

Referring to FIGS. 1, 2a and 2b, it will be seen that the equipment, in its first embodiment, consists of a cannula 1 fitted on an adaptor 2.

More precisely, the cannula 1, which is made of moulded plastic material exhibiting a certain elasticity, consists of a socket 3, presenting a cylindrical cavity 60, and of a rod 4 in which are formed two juxtaposed and parallel distribution channels 5 and 6, and of which the circular cross-section is constant over almost the whole of their length. The free end of the rod 4 is bevelled. The end of the channel 5 directed away from the socket 3 is narrowed in a profile 7 so that the jet of fluid sprayed from this channel 5 is deflected away from the longitudinal axis X—X' of the said channel 5 in the direction D—D' converging on the longitudinal axis Y—Y' of the channel 6. The end of the channel 6 directed away from the socket 3 is also narrowed in order to increase the outlet pressure. In the immediate vicinity of its free edge, the socket 3 is provided, on its inner face, with a series of elastically deformable projections 8.

The inner wall of the socket 3 has an axial rib 61 designed to penetrate into an axial recess 62 provided on the wall of the adaptor 2 in order to permit an appropriate and rapid mutual orientation of the two components.

The adaptor 2 is a machined metallic component having a part 9 of standard external geometry for connection to the cannula 1, and a part 10 of external geometry specific for the connection to a given syringe model, for example Adec or Hanau.

Looking at this in detail, it will be seen that the standard part consists of a cylindrical block 11 whose dimensions correspond to those of the cavity 60 of the socket 3, in such a way that this block 11 fits perfectly therein, the downstream end face 37 of the adaptor coming to bear against the bottom of the socket 3. The block 11 has a peripheral groove 12 designed to receive the projections 8 of the cannula 1. Beyond the groove 12, in the upstream direction, the block has a zone of greater diameter 13 which defines a shoulder 14 against which the free edge of the socket 3 abuts.

The specific part 10 of the adaptor 2 has a peripheral groove 70 in which is housed an O-ring seal 15, while the upstream end face 16 defines a cylindrical cavity 17.

Two fluid supply channels 18 and 19 pass through the adaptor 2. The longitudinal axis of the supply channel 18 coincides over the whole of its length with that X—X' of the distribution channel 5 of the cannula 1 when the latter is in position on the adaptor 2.

In contrast, the supply channel 19 comprises:

an upstream part 20 whose longitudinal axis Z1-Z2 coincides with the longitudinal axis of the cylindrical cavity 17, but not with the axis Y—Y' of the distribution channel 6 of the cannula 1, a downstream part 22 whose longitudinal axis coincides with the said axis Y—Y', and an intermediate merging part 21 between the parts 20 and 22.

This configuration obviously has the aim of compensating for the difference in axis between the syringe being fitted on the adaptor 2 and the standard cannula 1.

The supply channel 18 is in communication with the outside, at the upstream end, via an inlet passage 23 whose longitudinal axis W1-W2 forms an angle with the axis X—X'.

A tubular inlet sleeve 24 is immobilised in the upstream end of the supply channel 19 by partial penetration into the said channel, while tubular outlet sleeves 25 and 26 are immobilised respectively, in the same way, in the downstream end of the supply channels 18 and 19. The inlet sleeve 24 and outlet sleeves 25 and 26 thus project, respectively, from the upstream end face and the downstream end face of the adaptor 2.

An O-ring seal 27 is lodged around the tubular inlet sleeve 24 in the cylindrical cavity 17.

The tubular inlet sleeve 24 and the inlet passage 23 permit the connection of fluids with the syringe, and the tubular outlet sleeves 25 and 26, whose diameter is such that they can be introduced into the distribution channels 5 and 6 with slight force, ensure the communication of fluids with the cannula 1.

When it is desired to spray a mixture of air and water using the equipment according to the invention, the air is admitted via the inlet passage 23 and the supply channel 18, and the water via the supply channel 19. The profile 7 of the free end of the distribution channel 5 forces the jet of air to strike the jet of water emerging from the distribution channel 6 and to mix with this water.

It will be understood from the preceding description that the part 10 of the metallic adaptor 2 is designed to be joined to a syringe by means of which the distribution of fluids is controlled, the seals 15 and 27 ensuring the leakproofness of the connection. The part 9 of the adaptor receives and holds the disposable cannula 1, in particular by virtue of the engagement of the elastically deformable projections 8 in the groove 12, the leakproofness and a complementary retention being ensured by the penetration, with slight force, of the projecting part of the sleeves 25 and 26 into the distribution channels 5 and 6, this penetration being made possible by the at least slightly elastic nature of the material of the cannula.

The second embodiment in FIGS. 3 and 4a-c differs from that which has just been described essentially in the adaptor being composed of several parts and in the positioning of the access, at the upstream end, to the supply channels of the said adaptor.

The components in the second embodiment which are identical to those in the first embodiment will be designated by the same reference numbers and will not be described again, whereas the components which are similar will be designated by the same reference numbers, but followed by the "prime" sign.

As will be seen, the adaptor 2' consists of a muff 28 and a core 29.

The muff 28 comprises a standard part 9' and a specific part 10'. The standard part defines a block 11', in which a peripheral groove 12' is formed, and a zone of greater diameter 13' forming a shoulder 14' against which the free edge of the socket 3 of the standard cannula 1 abuts. The specific part 10' consists of a cylindrical block 31 of smaller diameter than the part 13'. The muff 28 defines a cylindrical cavity 32 of constant diameter.

The core 29 consists, on the one hand, of a cylindrical body 33 whose outer diameter corresponds, apart from introductory play, to the inner diameter of the cavity 32 of the muff 28 and, on the other hand, of a cylindrical part 34 of greater diameter defining a shoulder 43. The length of the cylindrical body 33 is such that, when the core is passed into the muff 28 until the shoulder 43 comes into abutment against the upstream end face 48 of the muff 28, the downstream end face 35 of the core 29 is flush with that 36 of the muff 28. These end faces 35 and 36 together correspond to the end face 37 of the adaptor 1 and, as such, come into abutment against the bottom of the socket 3 of the cannula 1 when the projections 8 of the latter are in engagement with the groove 12'.

Two supply channels 18' and 19' are formed in the core 29, each one in three parts, like the channel 19, namely an upstream part having a longitudinal axis, respectively W1'-W2' and Z1-Z2', parallel to the axes X—X' and Y—Y', but offset relative to the latter, a downstream part whose longitudinal axes coincide, respectively, with the said axes X—X' and Y—Y', and an intermediate merging part. In the upstream ends of the supply channels 18' and 19' there are immobilised, by partial penetration, tubular inlet sleeves 38 and 24', respectively, and, in the downstream ends of these same channels, tubular outlet sleeves 25', 26'.

In order to connect the adaptor 2' to the syringe, for example of the Lucciani type, and in order to retain the core 29 in the muff 28, a nut 39 is provided which has an upstream end face 40, a downstream end face 41 and a cavity 42. The cavity 42 defines an upstream cylindrical zone 43 and a downstream cylindrical zone 44 of smaller diameter, the junction between the zones 43 and 44 creating a shoulder 45 against which there bears the peripheral zone of the stop 43 which protrudes beyond the upstream end face 48 of the muff 28. The length of the downstream cylindrical zone 44 of the nut 39 corresponds to that of the cylindrical part 31 of the muff 28 so that, when the face 43 abuts on the faces 48 and 45, the downstream end face 41 of the nut 39 abuts against the upstream wall 49 of the zone of greater diameter 13' of the muff 28.

The upstream cylindrical zone 43 of the nut 39 is threaded at 46, which allows it to be screwed onto the syringe. When the adaptor 2' is thus joined to the syringe, the inlet sleeves 38 and 24' penetrate into corresponding conduits in the syringe.

As will be seen, from the upstream end face 50 of the core 29 there project, not only the tubular inlet sleeves 38 and 24', but also a corrector 51 designed to penetrate into a suitable orientation orifice provided in the syringe.

Although, in the present description, reference is made to the spraying of mixtures of fluids, it is understood that it is possible to spray only one fluid at a time, for example air: this is not associated with the equipment according to the invention, but to the control possibilities of the syringe.

We claim:

1. An attachment for a syringe for spraying mixtures of fluids, comprising:

(a) an adapter having an upstream end for being connected to the syringe, a downstream end, and two supply channels extending therethrough for receiving respective fluids;

(b) a disposable cannula molded of a plastic material and connected to the downstream end of said adapter, said cannula defining two longitudinally-extending distribution channels for communicating respectively with the two supply channels of said adapter to distribute the respective fluids from an upstream end of said cannula to a downstream end of said cannula, said distribution channels converging at the downstream end of said cannula to mix the fluids distributed therethrough;

(c) at least one tubular outlet sleeve connected to a respective one of said two supply channels and extending outwardly from a downstream end face of said adapter, said tubular outlet sleeve received in a corresponding one of said two distribution channels for promoting the passage of fluid from the one of said two supply channels to the one of said two distribution channels; and (d) at least one inlet passage communicating with a respective one of said two supply channels at an upstream end face of said adapter for directing fluid downstream through the respective one of said two supply channels.

2. An attachment for a syringe according to claim 1, wherein said at least one inlet passage extends parallel to the longitudinal axis of the adaptor.

3. An attachment for a syringe according to claim 1, wherein said at least one inlet passage extends at an angle with respect to the longitudinal axis of the adaptor.

4. An attachment for a syringe according to claim 1, wherein said cannula includes a connection socket for mating with a downstream end part of said adaptor, and further wherein the flow cross-sections of the respective two supply channels are substantially equal to the flow cross-sections of the respective two distribution channels.

5. An attachment for a syringe according to claim 4, wherein the inner face of the peripheral wall of said socket includes an axial rib, and the outer peripheral face of said adaptor includes a complementary-shaped axial recess for receiving said axial rib.

6. An attachment for a syringe according to claim 4, wherein the inner face of the peripheral wall of said socket includes a series of regularly spaced and elastically deformable projections, and the outer peripheral face of said adaptor includes a peripheral groove for receiving said projections.

7. An attachment for a syringe according to claim 6, wherein the adaptor further includes two tubular inlet sleeves communicating respectively with said two tubular outlet sleeves, and an orientation pin extending parallel to the longitudinal axis of the adaptor and projecting outwardly from an upstream end face of said adapter, and an orientation pin opening formed in said adaptor for receiving and holding said orientation pin.

8. An attachment for a syringe according to claim 7, wherein the adaptor further comprises a muff received in the socket of said cannula.

* * * * *